United States Patent [19]
Thornton et al.

[11] Patent Number: 6,048,300
[45] Date of Patent: Apr. 11, 2000

[54] COMPACT CARTRIDGE FOR AFTERLOADER

[75] Inventors: Richard T. Thornton, League City; Richard V. Calfee; John P. Edison, both of Houston; Kenneth M. Bueche, Friendswood; Edward N. Kite, Houston, all of Tex.

[73] Assignee: Guidant Corporation, Santa Clara, Calif.

[21] Appl. No.: 08/888,332

[22] Filed: Jul. 3, 1997

[51] Int. Cl.[7] .................................................. A61M 36/00
[52] U.S. Cl. .................. 600/7; 600/1; 600/3; 250/496.1; 250/497.1
[58] Field of Search .............................. 250/496.1, 497.1, 250/498.1; 600/1, 3, 7

[56] References Cited

U.S. PATENT DOCUMENTS

| | | |
|---|---|---|
| 3,638,524 | 2/1972 | Martin ....................................... 84/95.1 |
| 4,631,415 | 12/1986 | Sauerwein et al. . |
| 4,881,937 | 11/1989 | Van't Hooft et al. . |
| 5,030,194 | 7/1991 | Van't Hooft . |
| 5,092,834 | 3/1992 | Bradshaw et al. . |
| 5,503,041 | 4/1996 | Van't Hooft ............................ 74/502.6 |

*Primary Examiner*—Linda C. M. Dvorak
*Assistant Examiner*—Rosiland Kearney
*Attorney, Agent, or Firm*—Blank Rome Comisky & McCauley LLP

[57] ABSTRACT

A compact cartridge for an afterloader includes a housing containing a radioactive sourcewire and a dummy test wire, each accommodated in a helical groove on the periphery of a wire storage drum. The wires are contained in the grooves by low friction bearings, such as rollers, so that advancement of the wire from the drum is under very low friction conditions. The cartridge is removably inserted in the head of an afterloader apparatus and engages a primary drive system and an emergency retract mechanism mounted in the head. The cartridge also contains an electronics board with software for updating the software in the control electronics for the afterloader.

12 Claims, 6 Drawing Sheets

COMPACT CARTRIDGE FOR AFTERLOADER

BACKGROUND OF THE INVENTION

The present invention relates to a method of and an apparatus for the handling and precise positioning of radioactive sources used in radiation oncology and intravascular radiotherapy, particularly to a device known as an afterloader, which advances a wire or cable having a radioactive source at the tip along a catheter or other closed pathway to a position within the body of a patient for a predetermined period of time and which thereafter withdraws the wire and radioactive source from the patient.

It is known in the medical field to use afterloader devices in the treatment of cancerous tumors using radioactive sources having intensity greater than that which can safely be handled. Typically one or more catheters, needles, or other closed pathways (hereafter "catheters") to the treatment site are positioned in the patient. The catheters are then attached to the afterloader which advances the radioactive source at the end of the wire, sometimes called a sourcewire, along the catheters according to a predetermined sequence calculated to deliver a therapeutic dose of radiation to the tumor. Typical of the prior art apparatus are those disclosed in U.S. Pat. Nos. 4,631,415; 4,881,937; and 5,030,194. Many of these prior art devices advance the sourcewire by means of a friction drive belt trained about a wheel with the wire sandwiched between the belt and wheel.

Less well known but rapidly gaining acceptance is the use of radiation to prevent or inhibit restenosis following percutaneous transluminal coronary angioplasty (PTCA) or other arterial lumen opening procedure. PTCA, also known as balloon angioplasty, is the predominant treatment for coronary vessel stenosis. Approximately 300,000 procedures were performed in the United States (U.S.) in 1990 and an estimated 400,000 in 1992. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% of all patients requiring repeat PTCA procedures or by-pass surgery, with attendant high cost and added patient risk. More recent attempts to prevent restenosis by use of drugs, mechanical devices, and other experimental procedures have had limited success.

Restenosis occurs as a result of injury to the arterial wall during the lumen opening angioplasty procedure. In some patients, the injury initiates a repair response that is characterized by hyperplastic growth of the vascular smooth muscle cells in the region traumatized by the angioplasty. The hyperplasia of smooth muscle cells narrows the lumen that was opened by the angioplasty, thereby necessitating a repeat PTCA or other procedure to alleviate the restenosis.

Preliminary studies indicate that intravascular radiotherapy (IRT) has promise in the prevention or long-term control of restenosis following angioplasty. It is also believed that IRT may be used to prevent stenosis following cardiovascular graft procedures or other trauma to the vessel wall. A proposed IRT method disclosed in copending application Ser. No. 08/644,101 assigned to the assignee of this invention is first to advance a flexible catheter (radioguide catheter) through the cardiovascular system of the patient until the distal tip is at or near the region of the vessel that has been subjected to the angioplasty procedure. Subsequently, a sourcewire is advanced, preferably by an afterloader, along the radioguide catheter until the radiation source is disposed at the affected region. The radiation source is held at the affected region for a predetermined treatment period calculated to deliver an effective dose of radiation, then is withdrawn.

It will be appreciated from the foregoing that highly accurate positioning of the source within the patient is essential to maximize the effectiveness of the treatment while minimizing the damage to adjacent healthy tissue. It will also be appreciated that the source must be advanced to the treatment site as quickly as possible to minimize injury to healthy tissue along the catheter leading from outside the body of the patient to the treatment site.

To minimize trauma to sensitive tissue, the catheters and sourcewires that are used in sensitive areas are chosen to be as small as practicable, typically on the order of 0.5 millimeters. Use of these small diameter sourcewires presents special problems for the afterloader, for the small diameter wire does not have sufficient column strength to be driven into the catheter unless the afterloader design incorporates special precautions to prevent wire buckling. These problems associated with the potential buckling of the sourcewire are compounded by the need for rapid advancement of the sourcewire to avoid damaging healthy tissue.

With respect to the IRT application, in order to reach the site where the PTCA has been performed, the IRT sourcewire must often follow a tortuous pathway through the narrow twisted openings of the coronary arteries. In order to avoid blocking blood flow in these narrow openings, use of the smallest possible radioguide catheter and sourcewire is often required. If, however, the tiny radioguide catheter becomes kinked or otherwise obstructed as it is implanted, unless the obstruction is detected, the afterloader may drive the sourcewire through the wall of the catheter and even through the wall of the patient's blood vessel, with dire consequences. This problem is solved by the use of an active force feedback to enable the afterloader to drive a sourcewire through a catheter or other pathway at the highest possible speed without risk of puncturing a catheter or buckling the sourcewire as disclosed in copending U.S. patent application Ser. No. 08/436,075, the disclosure of which is incorporated herein by reference.

Another problem with prior art afterloaders is that the sourcewires in the afterloaders typically must be replaced by highly trained technicians. Such technicians must be periodically called upon to load the replacement sourcewire into the afterloader and verify the proper functioning of the afterloader system. In the case of short half-life sources, frequent replacement of sourcewires by skilled technicians obviously represents a significant cost in the maintenance of an afterloader. One solution to this problem is disclosed in the aforesaid copending U.S. application Ser. No. 08/436, 075. That solution involves the use of a replaceable modular "cassette" in which most of the components of the wire storage and wire drive systems are mounted in a cartridge that can be readily detached from the afterloader housing and replaced with a new cartridge. The sourcewire is loaded into the cartridge at the manufacturer and the proper operation of all the drive mechanisms, monitoring devices and other key components is verified by the manufacturer before the cartridge is delivered to the user. In this way, the cartridge can be installed in the afterloader at the user's facility by relatively unskilled persons with confidence that the afterloader system will function correctly.

It is important that such a replacement cartridge be relatively compact and lightweight for ease of handling, and have a rugged, highly reliable design to permit afterloader installation by unskilled persons and especially to minimize premature failures before sourcewire replacement is required.

SUMMARY AND OBJECTS OF THE INVENTION

Accordingly, it is a principal object of the present invention to provide a replaceable cartridge for an afterloader which includes a small, compact wire storage and drive system of exceptional ruggedness and reliability which incorporates a sourcewire and other key components of the afterloader that require service or replacement during the design life of the system or that require assembly, testing or verification by highly skilled technicians.

Another principal object of the invention is to provide a containment system for the wire stored on the wire storage drum of the wire storage and drive system which reliably and effectively contains the wire on the drum and permits rapid advancement and retraction of the wire with minimal friction.

Another important object of the present invention is to provide a compact afterloader replacement cartridge which contains the afterloader system software so that software updates are automatically provided for the afterloader and delivery system each time a sourcewire cartridge is replaced.

Another significant object of the present invention is to provide a compact sourcewire replacement cartridge for an afterloader which incorporates the mechanisms and performs the functions necessary to store a sourcewire and deliver it to the lumen of a catheter during, e.g., an IRT procedure, including active and inactive (dummy) wire storage/drive drums, a radiation safe, an emergency retract system, system software, and all other necessary sensing and monitoring components for the sourcewire.

A further important object of the present invention is to provide a wire storage and delivery mechanism that is substantially fail-safe and permits withdrawal of the sourcewire from a catheter in the patient being treated even in the event of failure of some or all of the wire storage drive components. This fail-safe capability is achieved by a unique arrangement of low friction bearing components for retaining the sourcewire in a helical groove of the sourcewire storage drum.

According to the present invention, a compact, replaceable cartridge for an afterloader is provided which contains an active sourcewire and radiation safe therefor, a combination sourcewire storage and drive drum mechanism that is characterized by a rugged and reliable design that requires no maintenance during the effective life of the radioactive source, and all necessary monitoring and testing devices. The cartridge includes two substantially identical wire storage and drive drums, one for the active sourcewire and one for an inactive or dummy test wire. Each drum is provided with a groove in its periphery for storing and guiding the advancement of the wire. Advantageously, the proximal end of each wire is anchored to its respective drum so that it can be advanced by rotating the drum and circumferentially retaining the wire in the groove of the drum with low friction elements, such as rollers or recirculating ball bearings. Thus, the sourcewire is always under a compressive load from its anchored proximal end to its distal end during the entire time it is advanced into the catheter.

The low friction elements for retaining the wire in the groove overcomes the wire spillage problems with the prior art devices which employ flexible friction belts to retain the wire on the drum. In the preferred embodiment, a plurality of rollers are mounted about substantially the entire periphery of the wire storage drum. The wire is thus positively prevented by the rollers from disengaging or spilling from its groove even under conditions of maximum wire advancement rate and maximum compressive force on the wire. The wire is urged radially outwardly against the roller surfaces during advancement resulting in a slight increase in the diameter of the wire loops in the groove of the drum. Any circumferential movement of the wire relative to the drum axis owing to that increase in diameter is substantially frictionless because the wire bears against the rollers.

A single primary drive mechanism is mounted in the afterloader apparatus housing and is selectively coupled to one or the other of the storage/drive drums in the replaceable cartridge for advancing a respective active or inactive wire into a catheter up to the treatment site. Emergency battery-powered and manual sourcewire retract mechanisms are mounted in the afterloader housing and are engageable with the active wire storage/drive drum for effecting withdrawal of the active sourcewire from the catheter upon a main power failure or primary drive failure.

BRIEF DESCRIPTION OF THE DRAWINGS

The above and other objects, aspects, features and attendant advantages of the present invention will become apparent from a consideration of the ensuing detailed description of presently preferred embodiments and methods thereof, taken in conjunction with the accompanying drawings, in which.

DETAILED DESCRIPTION OF PREFERRED EMBODIMENTS AND METHODS OF THE INVENTION

Figures 1, 12:
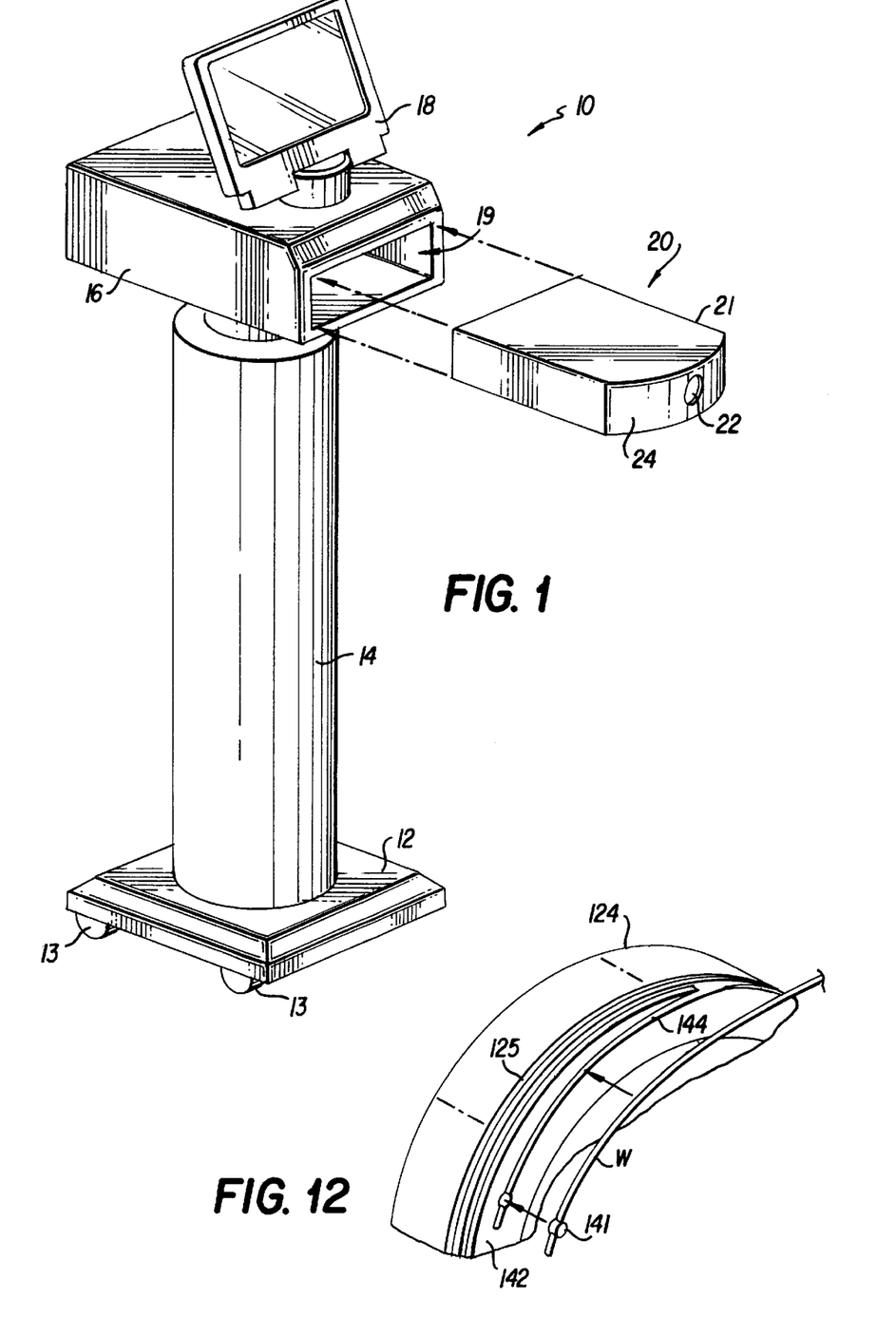
FIG. 1 is an exploded perspective view of an afterloader apparatus illustrating one embodiment of a replaceable sourcewire cartridge for use in the afterloader.
FIG. 12 is a fragmentary perspective view of one of the wire drums showing the manner in which a wire is anchored to the drum.

Referring now in detail to the drawings, there is illustrated in FIG. 1 an embodiment of an afterloader apparatus which is designated generally by reference numeral 10. Afterloader apparatus 10 comprises a base 12 which is preferably wheeled, a pedestal 14 and a head 16 which is vertically adjustable with respect to the pedestal 14 by means of an adjustment mechanism (not shown). An appropriate handle (not shown) may be mounted to the base or pedestal for use in positioning the apparatus 10 in a desired location. The head 16 may support a video monitor screen 18, such as an LCD touch screen display or the like. The front or forward end of the head 16 is provided with a receptacle opening 19 for removably receiving a replaceable cartridge or cassette 20. The cartridge 20 comprises a housing 21 with a sourcewire opening 22 in the front wall 24 thereof. As described in greater detail hereinafter, the cartridge 20 contains two elongate wires, namely, an active sourcewire and a dummy test wire, each stored on a respective storage/drive drum, a radiation shield or safe and necessary sensing, monitoring and software components of the system.

Replaceable cartridges 20 are preferably provided by the afterloader manufacturer or its distributor with all components loaded and tested so that when a cartridge is inserted into the receptacle opening 19 and mechanically and electrically engaged with the mating system connections in the head 16, the afterloader apparatus is ready for use in a medical procedure.

Preferably, the cartridge 20 also contains the system software so that software updates are automatically provided with each exchange of a cartridge. For that purpose, the afterloader apparatus contains a rewritable non-volatile program memory which is updated by the cartridge software. The replaceable cartridge of the invention permits the user to readily and safely exchange sourcewires as required by decay of the radioactive source without the assistance of highly skilled technicians.

Figure 2:
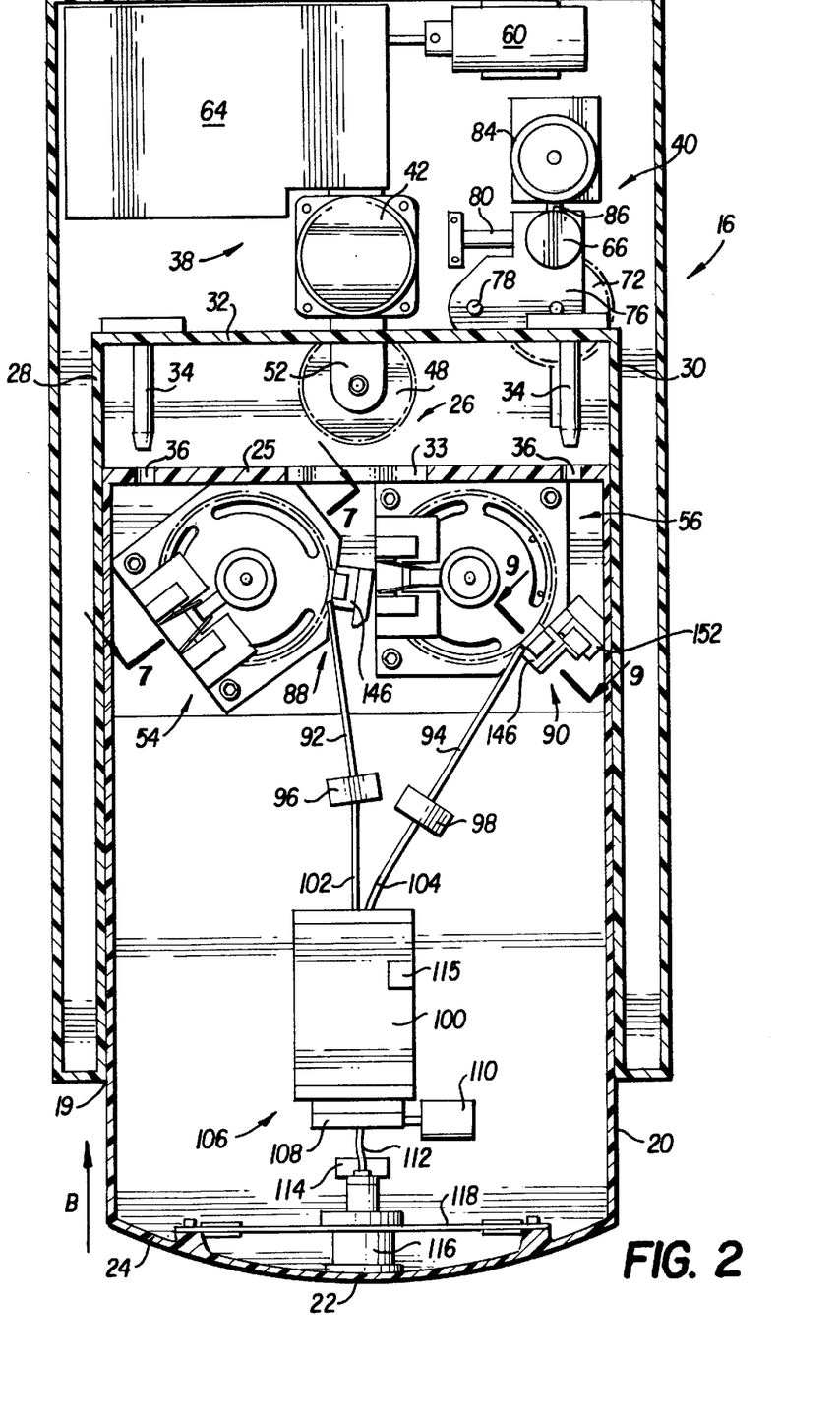
FIG. 2 is a top plan view partly in cross-section of the replaceable cartridge of FIG. 1 illustrating the manner of engagement between the cartridge components and the components of the afterloader apparatus.
Figure 3:
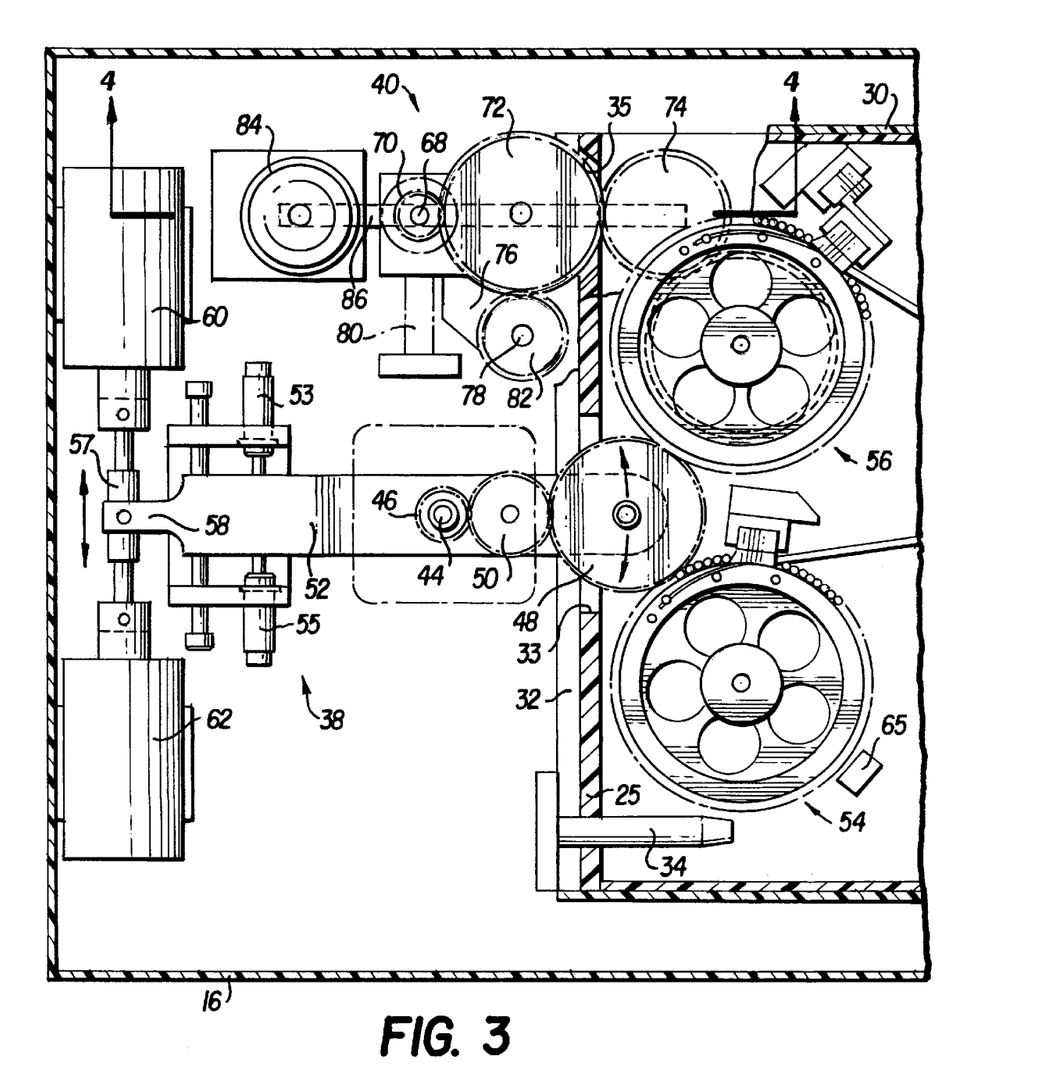
FIG. 3 is a partial top plan view, partly in cross-section, of the afterloader apparatus showing the primary drive system and emergency retract system engaged with the drive components of the replaceable cartridge.

FIGS. 2 and 3 are top views of the head 16 and the cartridge 20 illustrating the manner in which the cartridge is inserted into the receptacle opening 19 of the head in the direction of the arrow B (FIG. 2). The head 16 has a space or cavity 26 formed in part by side walls 28, 30 and end wall 32. A pair of tapered engagement pins 34 are mounted to the end wall 32 for mechanically engaging in a corresponding pair of holes 36 in the rear wall 25 of the cartridge and locating the cartridge in position as shown in FIG. 3. An electrical connection (not shown) between the cartridge electrical components and the electrical components of the afterloader control system (not shown) in the head is also made when the cartridge is fully inserted into the space 26. If desired, a sensor and indicator (not shown) may be provided for sensing when the cartridge 20 is fully engaged both mechanically and electrically into the head.

Mounted in the head 16 are the primary drive system 38 and the emergency retract system 40 which are engageable with cooperative components of the cartridge as explained in more detail hereinafter. The primary drive system 38 comprises a primary drive motor 42 with a vertically oriented output shaft 44 and spur gear 46 for driving a main drive gear 48 through an idle gear 50. Drive gear 48 is rotatably mounted at one end of an engagement arm 52 which is pivotable about the axis of the output shaft 44 of the drive motor 42 at a point intermediate the ends of the arm 52.

The rear wall 32 of the head has a central opening 33 for receiving the drive gear 48 and arm 52 when the cartridge 20 is placed fully inserted into the head 16 as shown in FIG. 3. When the cartridge 20 is fully inserted, the drive gear is located in a neutral position between the dummy drive unit 54 and the active drive unit 56 in the cartridge, but is not drivingly engaged with either unit upon insertion. Spring-biased plungers 53, 55 maintain the arm 52 in the neutral position.

The other end 58 of the engagement arm 52 is connected to a pair of solenoids 60, 62 by an actuating rod 57. The solenoids comprise a dummy drive solenoid 60 and an active drive solenoid 62 which pull the end 58 of arm 52 via rod 57 in opposite first and second directions, respectively, to pivot arm 52 about shaft 44 and thereby engage the drive gear 48 with either the dummy drive unit 54 or the active drive unit 56 as shown and described hereinafter in connection with FIG. 6. A power supply board 64 (FIG. 2) for the primary drive system 38 is mounted in the housing above the active drive solenoid 62. A brake 65 is provided on the dummy drive unit 54 to hold the dummy wire in the park or retracted position except during a treatment.

The emergency retract system 40 is used to retract the active sourcewire from a catheter either by means of battery power or manually in the event of a power failure or primary drive failure. Emergency retraction is necessary to avoid a radioactive overdose of the patient and operating personnel. System 40 comprises a battery-powered retract motor 66 with a vertically oriented shaft 68 upon which a spur gear 70 is mounted for driving a main gear 72. Main gear 72, in turn, meshes with retract gear assembly 74 mounted in the cartridge 20 when the cartridge is inserted into the head. An opening 35 (FIG. 3) in rear wall 32 of the cartridge accommodates main gear 72 and permits it to engage with retract gear assembly 74.

The retract motor 66 and main gear 72 are mounted on a plate 76 which is pivotable about the axis of a rotatable shaft 78. Plate 76 is forced by a spring 80 to rotate clockwise about shaft 78 so that gear 72 is biased into meshing engagement with retract gear assembly 74. A further gear 82 is mounted to shaft 78 and meshes with main gear 72. Shaft 78 extends through the top of housing 16 and is provided at its upper free end with a hand wheel (not shown) for manually retracting the sourcewire in the event of failure of both the primary drive system 38 and the emergency retract system 40.

A retract solenoid 84 operates a disengagement lever 86 to disengage the emergency retract system 40 from the active drive unit 56 only during a treatment of a patient. At all other times, including when there is a power failure or a drive failure, solenoid 84 is deenergized so that the emergency drive system is engaged with the active drive unit 56. Operation of the emergency retract system 40 is described in more detail hereinafter in connection with FIGS. 4 and 5.

In addition to the dummy drive unit 54 and active drive unit 56, the cartridge 20 also houses take-off mechanisms 88, 90 for the dummy wire (not shown) and the active sourcewire (not shown), respectively. As each wire is taken off the storage drive of its respective drive unit, it passes through a respective take-off tube 92, 94. Each take-off tube 92, 94 engages in a respective pivot block 96, 98 from which the wires are guided into separate, parallel passages in a radiation safe or source shield 100 by tubes 102, 104. A shutter mechanism 106 is provided on the outward end of shield 100 and includes a shutter 108 with a passage (not shown) and a shutter actuator 110 for positioning the shutter passage to connect either the active sourcewire or the dummy wire to the catheter path. A tube 112 connects the shutter passage to a home sensor unit 114 which precisely locates the distal tip of the dummy wire or active sourcewire. The home sensor unit 114 may include an optical, mechanical, inductive, capacitive or magnetic sensor which produces an output to the afterloader control system when the distal tip passes the home sensor unit either upon extension or retraction. Upon extension, the amount of wire extended can be measured and upon retraction, it can be determined that the entire wire has been retracted and that no wire breaks have occurred.

A radiation detector 115, such as a solid state radiation detector, is embedded in the radiation safe 100. When a new source calibration is entered into the control electronics, the detector 115 provides a coarse validation of the source activity. When the active sourcewire is advanced from the drive unit 56, the detector operation can be checked by observing a drop in the output of the detector. At the conclusion of a treatment, the detector 115 provides an indication that the entire source has been retracted to its proper position in the safe 100 and has not, for example, broken off in the catheter. The detector may also be used to verify source decay calculations made by the control electronics.

A catheter receiver assembly 116 is mounted to the inside front wall 24 of the housing 21. Assembly 116 receives and locks the catheter in place and provides a signal to the afterloader control system indicating that the catheter is attached to the cartridge. The catheter receiver assembly 116 also contains a scanner and electronics for decoding machine readable information on the catheter so that such information can be inputted into the afterloader control system as described in the aforesaid copending U.S. patent application Ser. No. 08/436,075. The catheter receiver assembly 116 may be connected to a force sensor 118 for sensing the force applied to the catheter by the wire during insertion of the wire. This sensed force may be used to control the insertion and insertion rate of the wire as described in the aforesaid copending U.S. patent application Ser. No. 08/436,075.

Figure 4:
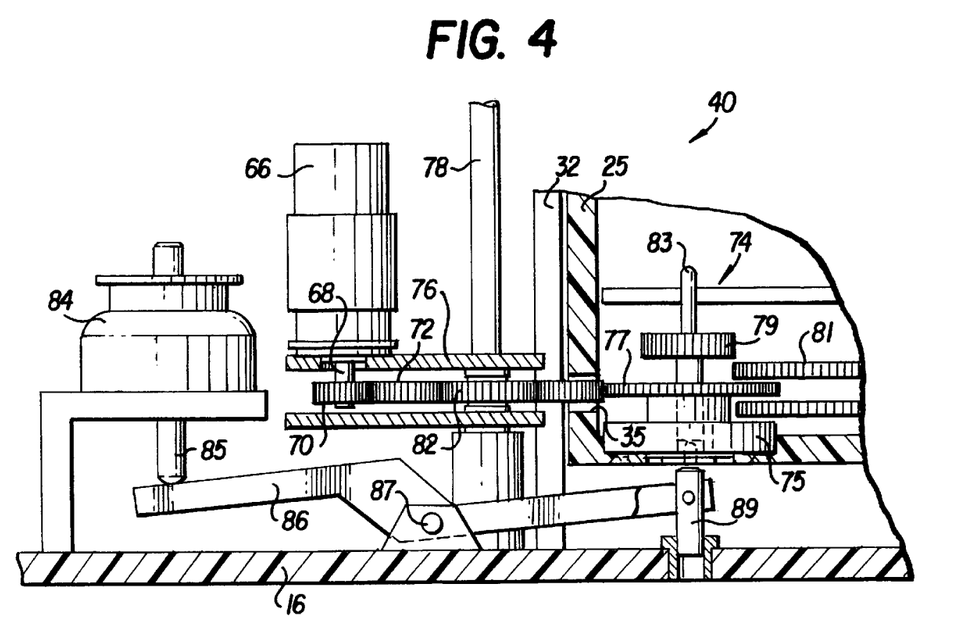
FIG. 4 is a fragmentary side elevation view of the emergency retract system taken along line 4—4 of FIG. 3 showing the emergency retract system in its disengaged position.
Figure 5:
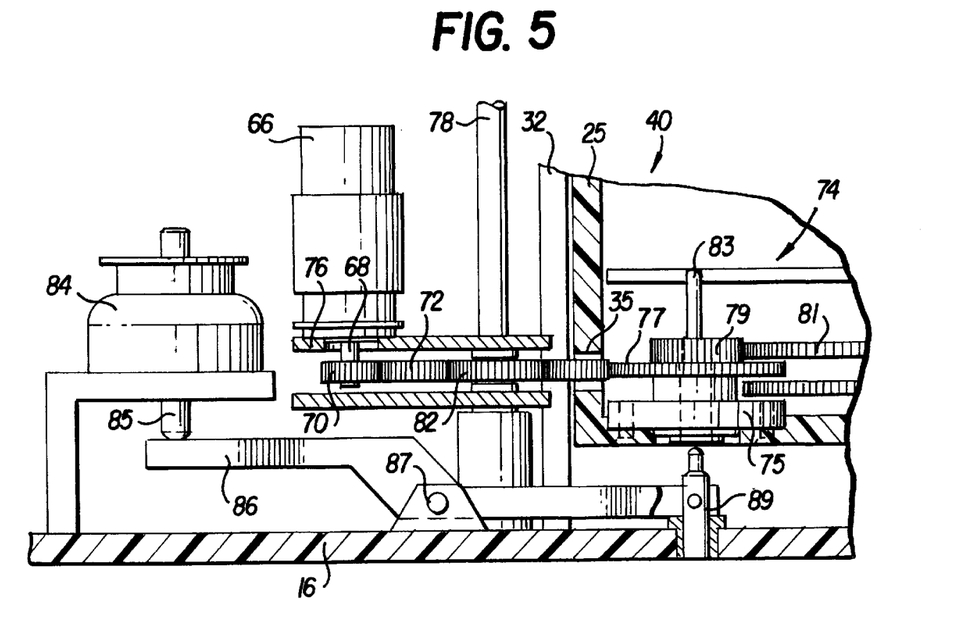
FIG. 5 is a fragmentary side elevation view of the emergency retract system taken along line 4—4 of FIG. 3 showing the emergency retract system in its engaged position.

Referring to FIGS. 4 and 5, there are illustrated the disengaged and engaged positions, respectively, of the emergency retract system 40. Retract gear assembly 74 is mounted in a unidirectional bearing 75 so as to permit rotation in only one direction, namely, the direction for withdrawing or retracting the active sourcewire from the catheter. The retract gear assembly 74 includes first and second retract gears 77, 79 with gear 79 splined to gear 77 so as to be axially (vertically) movable with respect thereto. In the position shown in FIG. 4, gear 79 is at its uppermost axial position disengaged from the retract reel gear 81 of the active drive unit 56. In the position shown in FIG. 5, gear 79 is at its lowermost axial position engaged with the retract reel gear 81. The gear 79 is fixedly mounted to a shaft 83 which may be spring-biased downwardly so as to urge the gear 79 toward its engaged position with retract reel gear 81.

As seen in FIG. 4, the retract solenoid 84 is energized since power is applied to the afterloader and a treatment is being performed. In this condition, the plunger 85 of the solenoid 84 pushes downwardly on the disengagement lever 86 which rotates counterclockwise about pivot pin 87 as viewed in FIG. 4, and forces drive pin 89 upwardly into engagement with shaft 83 thereby disengaging gear 79 from gear 81. So long as power is applied to the afterloader during a treatment, the emergency retract system 40 will remain in the position shown in FIG. 4 disengaged from the active drive unit 56. Should power be lost to the afterloader, or when no treatment is being performed, the solenoid 84 will be deenergized thus permitting the plunger 85 to retract to the position shown in FIG. 5. When that occurs, the disengagement lever 86 rotates clockwise about pivot pin 87 lowering drive pin 89 and permitting shaft 83 to move axially downwardly (optionally under the force of a spring) so that gear 79 of the retract gear assembly 74 engages with gear 81. Preferably, immediately upon loss of power to the afterloader, the battery (not shown) which supplies power to emergency retract motor 66 is automatically connected to the motor 66 by a solenoid switch or the like to cause the motor to rotate gear train 70, 72, 77, 79, 81 and retract the sourcewire from the catheter in the body of the patient. Should the battery or motor 66 be inoperative or defective, the afterloader operator may use the manual handwheel attached to shaft 78 to rotate gear train 82, 72, 77, 79, 81 and manually retract the sourcewire from the catheter. The unidirectional bearing 75 locks the drive in the fully retracted position at all times except during a treatment and also prevents manual operation of the emergency retract system in a direction to advance the sourcewire further into the catheter.

Figure 6:
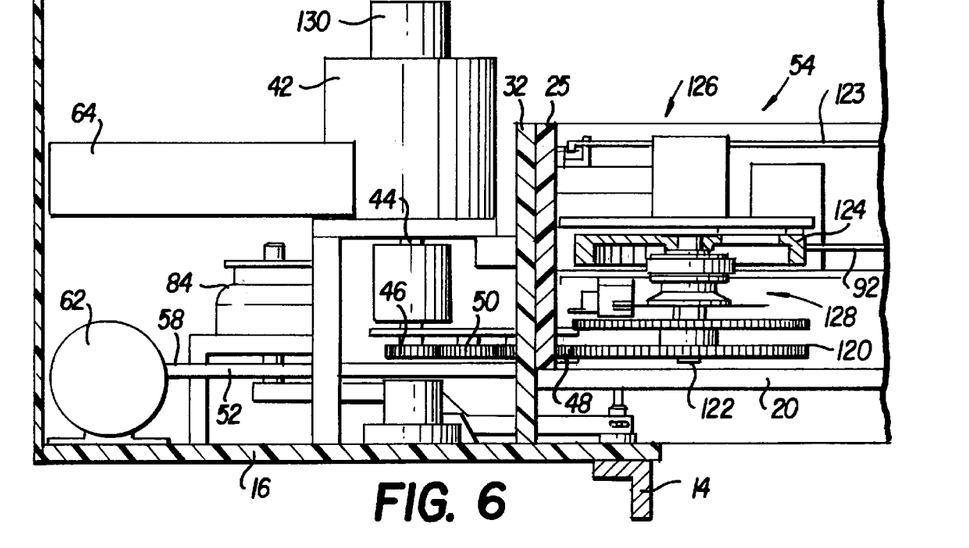
FIG. 6 is a fragmentary side elevation view of the primary drive system engaged with the dummy wire drive.

FIGS. 3 and 6 illustrate the manner in which the primary drive system 38 is connected to the dummy drive unit 54 which is substantially identical to the drive system connection to the active drive unit so that only one such connection need be described. With the cartridge 20 fully inserted into the head 16, the drive gear 48 is disposed in a neutral position between the primary reel gears 120 of the drive units 54, 56. When it is desired to drive the dummy drive unit 54, for example, solenoid 60 is energized which urges the end 58 of arm 52 upwardly as viewed in FIG. 3 and the gear 48 downwardly into engagement with gear 120.

Gear 120 is secured to the end of the drive shaft 122 for the dummy wire drive drum 124 which is shown and described in greater detail in connection with FIG. 6. When primary drive motor 42 is rotated in one direction, gear train 46, 50, 48, 120 rotates the dummy wire drum 124 to advance the dummy wire contained in the groove on the periphery of the drum 124 through tube 92 and into the catheter. When the motor 42 is rotated in the opposite direction, gear train 46, 50, 48, 120 rotates the drum 124 in the opposite direction to retract the dummy wire into the groove.

An electromechanical limit stop mechanism 126 is provided for limiting the number of revolutions of the drive drum 124 and therefore the maximum length of wire advanced into the catheter. The operation of the limit stop mechanism 126 is described in more detail hereinafter in connection with the description of FIGS. 7 and 8.

The drive shaft 122 is coupled to an encoder 128 which detects the incremental length of wire advanced from or retracted to the drum 124. A motor current sensor 130 may also be provided for sensing the current applied to the drive motor 42. Such sensor may be used to control the force applied to the sourcewire or dummy wire during advancement thereof in the manner described in copending U.S. patent application Ser. No. 08/436,075.

The cartridge 20 also includes an internal electronics board 123 which contains software from which the afterloader control system boots and which updates the control system software, e.g., a rewritable, non-volatile program memory, contained in the afterloader head 16.

FIGS. 7–12 illustrate the dummy drive unit 54 in greater detail. It should be understood that the dummy drive unit 54 and the active unit 56 are substantially identical in construction and operation and any significant differences will be specifically described herein.

Figures 7, 8:
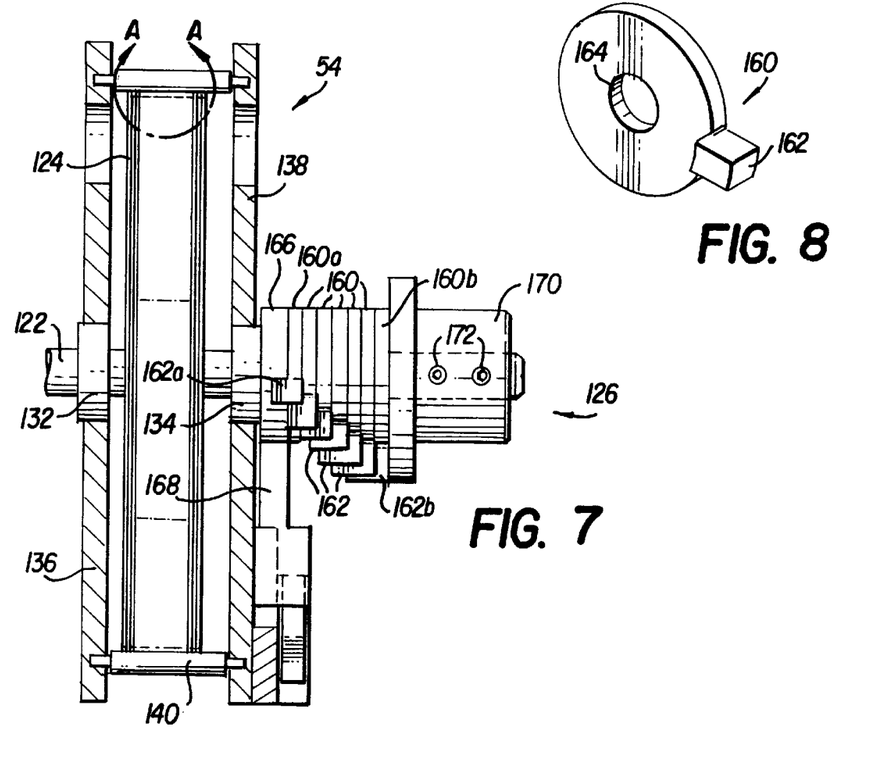
FIG. 7 is a side view, partly in cross-section, of the dummy drive taken along line 7—7 of FIG. 2 showing the grooved dummy wire drum and the limit stop mechanism for the dummy wire drum.
FIG. 8 is a perspective view of a washer of the limit stop mechanism of FIG. 7.

Drive unit 54 comprises drive drum 124 having a diameter of about 3 inches and a helical groove or thread 125 machined in the periphery thereof for storing a flexible wire W having a diameter of about 0.020 inch. The drum 124 is fixedly mounted on drive shaft 122 which is rotatably mounted in a pair of double or redundant bearings 132, 134 for rotation about the vertical axis of shaft 122. Double bearings 132, 134 are supported in a pair of plates 136, 138 which are mounted in the cartridge 20 in fixed, spaced relationship to one another by a plurality of posts (not shown). Double bearings are preferably used for each bearing 132, 134 so that if one of the bearings of a double being should fail, the drive will continue to function normally.

The wire W is contained in the helical groove 125 by a plurality of low friction elements such as rollers 140 (FIG. 11) which surround the drum 124 over substantially its entire circumference. The rollers 140 provide a low friction containment of the wire W in groove 125 such that, as the drum rotates in a direction to advance the wire into the catheter (i.e., unwinds the wire from the drum), the wire expands outwardly against the rollers 140. The proximal end 141 of the wire W is anchored to the drum along one face 142 thereof (FIG. 12) and enters the helical groove 125 from an arcuate groove 144 in face 142.

Figure 11:
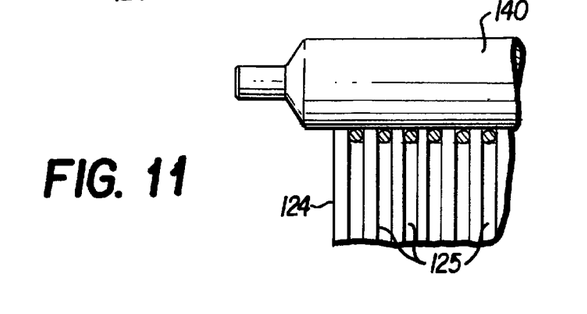
FIG. 11 is a fragmentary view shown as detail A—A in FIG. 7 illustrating the engagement between the rollers and the wire in the groove of the dummy storage and drive drum.

Because the wire is contained in the groove by the low friction rollers 140, the driving force of the drum 124 on the wire W acts from the proximal end 141 thereof and thus places the wire in compression along its entire length when the wire is driven into the catheter (i.e., unwound from the drum). Advantageously, the rollers 140 completely contain the wire W in the groove 125 with little or no slack in the wire along its path. Such tight containment of the wire positively prevents spillage of the wire from the drum which was possible in prior art belt drives.

Figure 9:
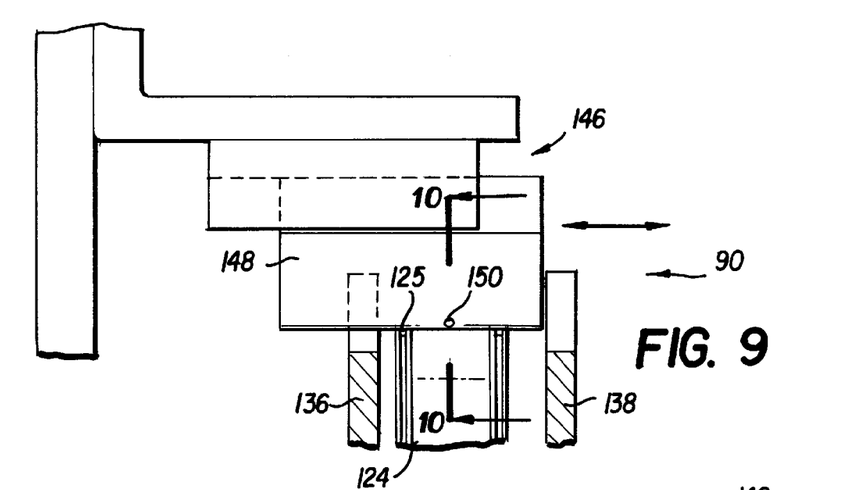
FIG. 9 is a cross-sectional detail view of the double slide wire guide mechanism for the active drive taken along line 9—9 of FIG. 2.
Figure 10:
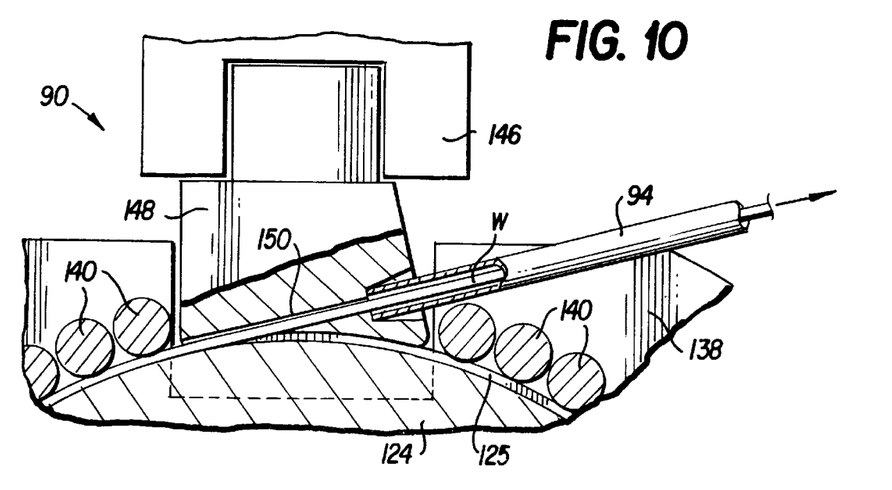
FIG. 10 is a fragmentary cross-sectional view taken along line 10—10 of FIG. 9 showing the details of the wire slide mechanism.

With reference to FIGS. 3, 9 and 10, the wire take-off mechanism 90 for the active sourcewire drive unit 56 will be described. Mechanism 90 comprises a slider block 148 made of a low friction material, such as UHMW plastic, which replaces several of the rollers 140. A hole 150 having a diameter slightly larger than the diameter of the wire W is drilled through the slider 148 along an axis tangential to the periphery of the drum 124. The slider 148 is mounted in a linear bearing 146 which permits the slider 148 to be moved by the wire W so that the slider 148 follows the helical groove 125 transversely across the drum periphery. One suitable linear bearing is made by the PIC Company of Middlebury, Conn. In the case of the take-off mechanism 90 for the active sourcewire drive unit 56, the slider 148 is supported in a pair of linear bearings 146, 152 (FIG. 2) so that if one of the bearings should seize or otherwise fail, the other bearing will still permit the slider to move under the force of the wire being payed off the drum. As shown in FIG. 2, the dummy drive unit 54 has only a single linear bearing 146 although two such bearings could be provided if desired.

Take-off pivot tube 94 (FIG. 10) engages in a tapered bore 156 of the slider 148 so that as the slider moves across the drum periphery, the take-off tube 94 pivots in the bore 156 as the slider 148 follows the helical groove 125 in the drum. The take-off tube 94 also pivots with respect to a tapered bore (not shown) in pivot block 98 from which the wire W passes through tube 104, shield 100 and tube 112 into the catheter receiver 116. The wire take-off mechanism 88 for the dummy drive unit 54 operates in the same way as take-off mechanism 90 for the active drive unit 56.

The limit stop mechanism 126 (FIG. 7) comprises a stack of washers 160 each having an overhanging tang or tab 162 and a central bore 164 (FIG. 8). A bearing sleeve (not shown) is provided on the shaft 122 for receiving the bores 164 of the washers so that undesired lockup between the washers will not seize the drive shaft 122. The washers 160 are stacked on a switch lever 166 which is rotatably mounted on the bearing sleeve of shaft 122. Lever 166 has a lever arm 168 which engages the tang 162a of the lower most washer 160a. An upper stop cap 170 is fixed to the upper end of the shaft 122 by means of set screws 172 and is provided with an overhanging tang (not shown) which engages the tang 162b of the uppermost washer 160b.

As the shaft rotates in one direction or the other, the tangs 162 engage one another seriatim from tang 162b to tang 162a. Tang 162a engages the lever arm 168 of switch lever 166 to rotate against spring force until one of a pair of microswitches 174 is operated. Each microswitch 174 transmits a signal to the afterloader control system electronics to indicate that the wire W has reached the limit of its travel in that direction or to control the primary drive system 38. It will be appreciated by those skilled in the art that the stop positions for advancing and retracting the wire W can be adjusted for any given or desired wire length by varying the number of washers 160 on the shaft and by adjusting the angular position of the overhanging tang on the upper stop cap 170.

Although certain presently preferred embodiments of the present invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A replaceable cartridge adapted to be inserted into a receptacle of afterloader apparatus to be placed in operative relation to a primary drive mechanism of the afterloader apparatus for selectively advancing an elongate wire having a radioactive source affixed to a distal end of the wire from said cartridge into and out of a catheter implanted in a patient, and to be readily removed from said receptacle and said operative relation to said primary drive mechanism of the afterloader apparatus when said cartridge is to be replaced, said replaceable cartridge comprising:

a housing adapted to receive a proximal end of the catheter;

said radioactive source wire positioned in said housing;

a secondary drive mechanism mounted in said housing for entering into said operative relation to said primary drive mechanism when said cartridge is inserted into said receptacle of said afterloader apparatus said secondary drive mechanism including a first wire storage drum having a rotational axis and a periphery with a groove formed therein for receiving said radioactive source wire, said radioactive source wire being wound and affixed to said first storage drum at a proximal end of said radioactive source wire so as to maintain a compressive force from end to end on said radioactive source wire during unwinding thereof from said first storage drum; and a plurality of low friction elements mounted about the periphery of said first storage drum adjacent said groove for maintaining free-rolling contact against said radioactive source wire and said first storage drum for tight low-friction containment of said radioactive source wire in said groove during unwinding from the drum under said compressive force and into said catheter when said catheter is received in said housing;

said secondary drive mechanism of the cartridge being selectively engageable with said primary drive mechanism of the afterloader apparatus after said cartridge is inserted in said receptacle whereby to selectively rotate said drum to advance or retract said radioactive source wire therein via said groove and thereupon into or out of said catheter when said catheter is received in said housing.

2. The replaceable cartridge of claim 1, wherein each of said plurality of low friction elements comprises a roller having an axis of rotation, the axes of rotation of the plurality of rollers being arranged parallel to the rotational axis of the drum.

3. The replaceable cartridge of claim 1, wherein said secondary drive mechanism further includes a second wire storage drum having a rotational as and a periphery with a groove formed therein for receiving a dummy wire to be advanced into and retracted from said catheter when said catheter is received in said housing, said dummy wire being wound and affixed at a proximal end thereof to said second drum so as to maintain a compressive force from end to end on said dummy wire during unwinding thereof from the second storage drum;

a plurality of low friction elements mounted about the periphery of said second storage drum adjacent the groove thereof for maintaining free-rolling contact against said dummy wire and said second storage drum for tight low-friction containment of the dummy wire in the groove during unwinding from said second storage drum under said compressive force into the catheter then said catheter is received in said housing; and said secondary drive mechanism of the cartridge being selectively engageable with said primary drive mechanism of the afterloader apparatus after said cartridge is inserted in said receptacle so as to selectively rotate either one of said first and second wire storage drums to advance or retract either said radioactive source wire or said dummy wire from or into the respective storage drum via the groove thereof and thereupon into or out of said catheter when said catheter is received in said housing.

4. The replaceable cartridge of claim 3, wherein each of said plurality of low friction elements comprises a roller having an axis of rotation, the axes of rotation of the plurality of rollers associated with said first drum being arranged parallel to the rotational axis of the first drum, and the axes of rotation of the plurality of rollers associated with said second drum being arranged parallel to the rotational axis of the second drum.

5. The replaceable cartridge of claim 3, wherein said cartridge includes an electronics board mounted in said housing for interaction with control system software of the afterloader apparatus, said electronics board containing means for updating the control system software.

6. The replaceable cartridge of claim 3, wherein the grooves in said drums are helical grooves and including a slider for taking off the wire from the groove of a respective drum, each slider being mounted in at least one linear bearing for movement transversely across the periphery of its respective drum, the wire in each groove passing through a hole in the slider associated therewith so that such slider takes the wire off its associated drum as such drum is rotated.

7. The replaceable cartridge of claim 3, including a radiation-shielding safe mounted in said housing, means for guiding said radioactive source wire from said first storage drum to the radiation-shielding safe, and a radiation detector in the radiation-shielding safe for detecting the presence of said radioactive source of said radioactive source wire in the radiation-shielding safe.

8. The replaceable cartridge of claim 3, including limit stop means associated with each of said first and second wire storage drums for limiting the number of revolutions thereof when selectively driven by said secondary drive mechanism, each of said limit stop means comprising a stack of washers mounted concentrically to the rotational axis of the respective drum, each washer having an overhanging tang engageable with the tang of an adjacent washer, at least one of said washers being operative to actuate a first switch in a first direction of rotation of the respective drum and a second switch in a second direction of rotation of the respective drum, the switches being operative to indicate or control the number of revolutions of the respective drum in each direction.

9. The replaceable cartridge of claim 1, including means mounted in said housing for engaging said first storage drum with an emergency retract mechanism of the afterloader apparatus when said cartridge is inserted in said receptacle, for rotating said first storage drum so as to retract said radioactive source wire from the catheter in response to a loss of electrical power to said afterloader apparatus.

10. The replaceable cartridge of claim 9, wherein said emergency retract mechanism engaging means automatically engages the emergency retract mechanism with said first storage drum in response to loss of electrical power to said afterloader apparatus.

11. The replaceable cartridge of claim 10 wherein said emergency retract mechanism engaging means includes a solenoid which, when actuated, selectively engages and disengages the emergency retract mechanism from said first storage drum.

12. The replaceable cartridge of claim 9, including guide means on said housing for guiding said housing into mating position in said receptacle of the afterloader apparatus for placing said secondary drive mechanism in operative relation to said primary drive mechanism and said emergency retract mechanism of the afterloader apparatus.

* * * * *